(12) United States Patent
Claverie et al.

(10) Patent No.: US 9,279,162 B2
(45) Date of Patent: Mar. 8, 2016

(54) BACTERIA AND THE USES THEREOF

(75) Inventors: Jean-Michel Claverie, Cassis (FR); Jacques Biton, Lacroix-Saint-Ouen (FR); Jean-Paul Leonetti, Castelnau-le-Lez (FR)

(73) Assignees: DEINOVE, Paris (FR); CENTRE NATIONAL DE LA RECHERCHE SCIENTIFIQUE (CNRS), Paris (FR); UNIVERSITE MONTPELLIER 1, Montpellier (FR)

( * ) Notice: Subject to any disclaimer, the term of this patent is extended or adjusted under 35 U.S.C. 154(b) by 0 days.

(21) Appl. No.: 13/600,596

(22) Filed: Aug. 31, 2012

(65) Prior Publication Data

US 2013/0045482 A1 Feb. 21, 2013

Related U.S. Application Data

(63) Continuation-in-part of application No. PCT/EP2011/053089, filed on Mar. 2, 2011.

(60) Provisional application No. 61/309,931, filed on Mar. 3, 2010.

(30) Foreign Application Priority Data

Mar. 2, 2010 (EP) .................................... 10305212

(51) Int. Cl.

| | | |
|---|---|---|
| *C12P 21/04* | (2006.01) | |
| *C12N 1/20* | (2006.01) | |
| *C12R 1/01* | (2006.01) | |
| *C12N 13/00* | (2006.01) | |
| *C12P 7/10* | (2006.01) | |
| *C12P 7/40* | (2006.01) | |
| *C12N 15/01* | (2006.01) | |
| *C12P 21/06* | (2006.01) | |
| *C12Q 1/02* | (2006.01) | |
| *C12Q 1/04* | (2006.01) | |
| *C12Q 1/24* | (2006.01) | |
| *C12Q 1/68* | (2006.01) | |

(52) U.S. Cl.
CPC ... *C12R 1/01* (2013.01); *C12N 1/20* (2013.01); *C12N 13/00* (2013.01); *C12P 7/10* (2013.01); *C12P 7/40* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 6,102,690 A | 8/2000 | Ingram et al. |
|---|---|---|
| 2011/0104766 A1 | 5/2011 | Leonetti et al. |
| 2011/0294979 A1 | 12/2011 | Leonetti et al. |
| 2011/0306085 A1 | 12/2011 | Isop et al. |
| 2012/0052540 A1 | 3/2012 | Biton et al. |
| 2012/0058533 A1 | 3/2012 | Biton et al. |

FOREIGN PATENT DOCUMENTS

| CN | 101591630 | 12/2009 |
|---|---|---|
| KR | 100836093 | 6/2008 |
| WO | WO 95/27064 | 10/1995 |
| WO | WO 97/10352 | 3/1997 |
| WO | WO 01/23526 | 4/2001 |
| WO | WO 02/059351 | 8/2002 |
| WO | WO 2006/131734 | 12/2006 |
| WO | WO 2007/128338 | 11/2007 |
| WO | WO 2009063079 A1 * | 5/2009 |
| WO | WO 2010/081899 | 7/2010 |
| WO | WO 2010/094665 | 8/2010 |
| WO | WO 2010/130806 | 11/2010 |
| WO | WO 2010/130812 | 11/2010 |
| WO | WO 2011107506 A1 * | 9/2011 |

OTHER PUBLICATIONS

Weon et al. (*Deinococcus cellulosilyticus* sp. nov., isolated from air, International Journal of Systematic and Evolutionary Microbiology (Aug. 2007), 57, 1685-1688.*
NCBI Accesion No. DQ883809 (Sep. 12, 2006).*
Basim (Pulsed-Field Gel Electrophoresis (PFGE) Technique and its use in Molecular Biology, Turk J Biol 25 (2001) 405-418).*
Rainey et al. (Phylogenetic Diversity of the Deinococci as Determined by 16s Ribosomal DNA Sequence Comparison, International Journaolf Systematic Bacteriologayp, r. 1997, p. 510-514).*
Rainey et al. Extensive Diversity of Ionizing-Radiation Resistant Bacteria Recovered from Sonoran Desert Soil and Description of Nine New Species of the Genus *Deinococcus* Obtained from a Single Soil Sample, Applied and Environmental Microbiology, Sep. 2005, p. 5225-5235).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Hirsch et al., "*Deinococcus frigens* sp. nov., *Deinococcus saxicola* sp. nov., and *Deinococcus marmoris* sp. nov., Low Temperature and Draught-tolerating, UV-resistant Bacteria from Continental Antarctica" 27 Systemic and Applied Microbiology 636-645 (2004).*
Lipton et al., "Global Analysis of the Deinococcus radiodurans proteome by using accurate mass tags" 99(17) Proceedings of the National Academy of Sciences USA 11049-11054 (2002).*

(Continued)

*Primary Examiner* — Nancy J Leith (74) *Attorney, Agent, or Firm* — Saliwanchik, Lloyd & Eisenschenk (57) ABSTRACT

The present invention relates to novel bacteria and the uses thereof. The invention particularly relates to *Deinococcus* bacteria and their use in the pharmaceutical or agro-chemical industries, e.g., for degrading biomass and/or producing metabolites or drugs of industrial interest.

14 Claims, 3 Drawing Sheets

(56) References Cited

OTHER PUBLICATIONS

Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.
Alea, F. et al. "Selection of hypercellulolytic derepressed mutants of *Cellulomonas* sp." *Applied Microbiology and Biotechnology*, 1991, pp. 643-645, vol. 35, No. 5.
Temp, U. et al. "A Small-Scale Method for Screening of Lignin-Degrading Microorganisms" *Applied Environmental Microbiology*, Apr. 1998, pp. 1548-1549, vol. 64, No. 4.
Zenoff, V. F. et al. "Diverse UV-B Resistance of Culturable Bacterial Community from High-Altitude Wetland Water" *Current Microbiology*, May 1, 2006, pp. 359-362, vol. 52, No. 5.
Pavlikova, E. et al. "Improvement of the Basidiomycete *Coprinus* sp." *Folia Microbiologica*, Jan. 1, 1982, pp. 126-130, vol. 27, No. 2.
Written Opinion in International Application No. PCT/EP2010/051885, Aug. 23, 2010, pp. 1-10.
Brim, H. et al. "Engineering *Deinococcus radiodurans* for metal remediation in radioactive mixed waste environments" *Nature Biotechnology*, Jan. 2000, pp. 85-90, vol. 18, XP-002491111.
Henstra, A. M. et al. "Microbiology of synthesis gas fermentation for biofuel production" *Current Opinion in Biotechnology*, 2007, pp. 200-206, vol. 18, XP-22110181.
John, R. P. et al. "Fermentative production of lactic acid from biomass: an overview on process developments and future perspectives" *Appl. Microbiol. Biotechnol.*, 2007, pp. 524-534, vol. 74, XP-002464997.
Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.
Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.
Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.
Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.
Smith, M. D. et al. "Gene expression in *Deinococcus radiodurans*" *Gene*, 1991, pp. 45-52, vol. 98, XP-002938523.
Zahradka, K. et al. "Reassembly of shattered chromosomes in *Deinococcus radiodurans*" *Nature*, Oct. 5, 2006, pp. 569-573, vol. 443, XP-002491114.
Office Action dated Nov. 8, 2012 in U.S. Appl. No. 12/740,404.
Fontaine, L. et al. "Molecular Characterization and Transcriptional Analysis of adhE2, the Gene Encoding the NADH-Dependent Aldehyde/Alcohol Dehydrogenase Responsible for Butanol Production in Alcohologenic Cultures of *Clostridium acetobutylicum* ATCC 824" *Journal of Bacteriology*, Feb. 2002, pp. 821-830, vol. 184, No. 3.
Skory, C. D. "Isolation and Expression of Lactate Dehydrogenase Genese from *Rhizopus oryzae*" *Applied and Environmental Microbiology*, Jun. 2000, pp. 2343-2348, vol. 66, No. 6.

Berdy, J. "Bioactive Microbial Metabolites—A personal view" *Journal of Antibiotics*, Jan. 1, 2005, pp. 1-26, vol. 58, No. 1.
Singh, S. et al. "Biodiversity, chemical diversity and drug discovery" *Progress in Drug Research*, 2008, pp. 142-174, vol. 65.
Yang, B. et al. "Effects of microwave irradiation on isolation of soil actinomycetes" *Yingyong Shengtai Xuebao*, May 2008, pp. 1091-1098, vol. 19, No. 5.
Sinha, R. et al. "UV-protectants in cyanobacteria" *Plant Science*, Dec. 23, 2007, pp. 278-289, vol. 174, No. 3.
Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.
Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.
Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.
Keller, M. et al. "Tapping Into Microbial Diversity" *Nature Reviews*, Feb. 2004, pp. 141-150, vol. 2, No. 2.
Reichenbach, H. "Myxobacteria, producers of novel bioactive substances" *Journal of Industrial Microbiology & Biotechnology*, Jan. 1, 2001, pp. 149-156, vol. 27. No. 3.
Bibb, M. "Regulation of secondary metabolism in streptomycetes" *Current Opinion in Microbiology*, 2005, pp. 208-215, vol. 8, No. 2.
Written Opinion in International Application No. PCT/EP2010/050513, Apr. 24, 2010, pp. 1-10.
Kolari, M. et al. "Colored moderately thermophilic bacteria in paper-machine biofilms" *Journal of Industrial Microbiology and Biotechnology*, Apr. 2003, pp. 225-238, vol. 30, No. 4.
Written Opinion in International Application No. PCT/EP2010/056600, May 14, 2009, pp. 1-8.
Anonymous. "Conference de presse: Présentation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10, XP-002591932.
Written Opinion in International Application No. PCT/EP2010/056592, Jul. 29, 2010, pp. 1-7.
Written Opinion in International Application No. PCT/EP2008/065613, Jan. 28, 2009, pp. 1-8.
Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.
Ferreira, A. et al. "*Deinococcus geothermalis* sp. nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4.
Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.

\* cited by examiner

```
SEQUENCE LISTING

<160> NUMBER OF SEQ ID NOS: 2

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
gttacccgga atcactgggc gta                                          23

<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2
ggtatctacg cattccaccg cta                                          23
```

BACTERIA AND THE USES THEREOF

CROSS-REFERENCE TO RELATED APPLICATIONS

This application is a continuation-in-part of International Application No. PCT/EP2011/053089, filed Mar. 2, 2011, which claims the benefit of U.S. Provisional Patent Application 61/309,931, filed Mar. 3, 2010, the disclosures of which are hereby incorporated by reference in their entirety, including all figures, tables and amino acid or nucleic acid sequences. PCT/EP2011/053089 also claims priority to European Patent Application Serial Number 10305212.2, filed Mar. 2, 2010, the disclosure of which is also hereby incorporated by reference in its entirety, including all figures, tables and amino acid or nucleic acid sequences.

FIELD OF THE INVENTION

The present invention relates to novel bacteria and the uses thereof. The invention particularly relates to *Deinococcus* bacteria and their use in the pharmaceutical or agro-chemical industries, e.g., for degrading biomass and/or producing metabolites or drugs of industrial interest.

BACKGROUND

The conversion of lignocellulosic biomass has been the subject of intense research efforts since the 1970s (Blumer-Schuette et al., 2008, Extremely thermophilic microorganisms for biomass conversion: status and prospects, Curr Opinion Biotechnol 19, pp. 210-217; Perez et al., 2002, Int Microbiol 5, pp 53-63). It is believed, however, that future biofuels or bioenergy products should originate from raw lignocellulosic biomass, instead of from agricultural feedstocks.

WO2009/063079 describes the use of stress-resistant bacteria such as *Deinococcus* bacteria for the production of bioenergy products and metabolites through degradation and fermentation of biomass. WO2010081899, unpublished at the priority date of the present application, discloses the ability of bacteria such as *Deinococcus* bacteria to produce valuable drugs, including antibiotics.

By pursuing their research towards the identification of bacteria having improved properties, the inventors have identified and isolated a particular bacterium of the *Deinococcus* species, termed M1-3H. This bacterium was isolated and selected by the inventors based on its remarkable ability to degrade biomass components and to generate metabolites. By analysing this bacterium in more details, the inventors have surprisingly found that its genome was very large, i.e., above 4 megabases long (Mb), in comparison to the genome size of classical *Deinococcus* bacterium. Indeed, the average size of the genome of a *Deinococcus* bacterium is around 3.0 Mb. Furthermore, the inventors have also surprisingly found that the genome of this bacterium contains a substantial degree of genomic diversity, i.e., substantial level of genetic material acquired by genetic transfer from diverse other species.

Several bacteria of the genus *Deinococcus* have been sequenced: *Deinococcus radiodurans* (White O et al., *Science* 1999 Nov. 19; 286(5444):1571-7), *Deinococcus geothermalis* (Makarova K S et at PLoS One. 2007 Sep. 26; 2(9):e955) and *Deinococcus deserti* (De Groot A. et al., *PLoS Genet.* 2009 March; 5(3): c1000434). None of these bacteria exhibit the properties of M1-3H.

The present invention thus describes, for the first time, the existence of bacteria related to *Deinococcus* having the unexpected properties (1) to display a genome substantially larger than the known *Deinococcus* species, and (2) to have acquired genetic diversity from diverse other species. The present invention also describes, for the first time, the existence of bacteria related to *Deinococcus* having the unexpected properties (1) to display a genome substantially smaller than the known *Deinococcus* species, and (2) to have acquired genetic diversity from diverse other species. These bacteria, as well as their uses, represent the subject matter of the present invention.

SUMMARY OF THE INVENTION

The present invention relates to novel bacteria, methods for their isolation and culture, as well as the uses thereof, particularly in the pharmaceutical and agro-chemical industries, e.g., to transform lignocellulosic biomass or derivatives thereof into valuable products, including fermentable sugars and bioenergy products, to produce drugs or as detoxifiers.

An object of this invention is an isolated bacterium, wherein said bacterium has a genome size above 3.9 megabases or below 2.9 megabases, and wherein said bacterium (i) contains a 16S rDNA which, upon amplification using primers GTTACCCGGAATCACTGGGCGTA (SEQ ID NO: 1) and GGTATCTACGCATTCCACCGCTA (SEQ ID NO: 2), generates a fragment of about 158 base pairs and/or (ii) resists a UV treatment of 4 mJ/cm$^2$. In certain embodiments of this object of the invention, the isolated bacterium can have a genome size ranging from: at least 3.9 megabases to 10 megabases; at least 4 megabases to 8 megabases; or at least 5 megabases to 7.5 megabases. In certain embodiments of this object of the invention, the isolated bacterium can also have a genomic diversity resulting from gene transfer that is greater than 15%, greater than 25%, greater than 50% or a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. Other embodiments within this object of the invention provide an isolated bacterium having a genomic diversity resulting from gene transfer that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

A further object of this invention is an isolated bacterium, wherein said bacterium contains a 16S rDNA which, upon amplification using primers GTTACCCGGAATCACTGGGCGTA (SEQ ID NO: 1) and GGTATCTACGCATTCCACCGCTA (SEQ ID NO: 2), generates a fragment of about 158 base pairs, and wherein the genome of said bacterium comprises a genomic diversity resulting from gene transfer that is greater than 15%, greater than 25%, greater than 50% or a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. Other embodiments within this object of the invention provide an isolated bacterium having a genomic diversity resulting from gene transfer that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

A further object of this invention is an isolated bacterium, wherein said bacterium contains a 16S rDNA which, upon amplification using primers GTTACCCGGAAT-CACTGGGCGTA and GGTATCTACGCATTCCAC-CGCTA, generates a fragment of about 158 base pairs, and wherein the genome of said bacterium comprises a genomic diversity resulting from gene transfer that is greater than 15%, greater than 25%, greater than 50% or a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. Other embodiments within this object of the invention provide an isolated bacterium having a genomic diversity resulting from gene transfer that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

Particular additional characteristics of the bacteria of this invention include any one, several, or all of the following:

the bacterium further comprises a recombinant nucleic acid molecule, the bacterium is resistant to stress, the bacterium is mesophile or thermophile, the bacterium is viable at a pH comprised between 4 and 9, the bacterium is viable in the presence of 2% ethanol, the bacterium can be grown in aerobiosis or in anaerobiosis, and/or the bacterium can utilize lignin, cellulose, hemi-cellulose, starch, xylan, polysaccharide, xylose, saccharose, or glucose, or derivatives thereof, as carbon source.

The bacterium is preferably a *Deinococcus* bacterium, or a bacterium the genome of which comprises a portion representing at least 60%, preferably at least 65, 70, 75, 80 or 85% of the total genome that can hybridize (under stringent conditions) with the genome of a *Deinococcus radiodurans* or *Deinococcus geothermalis*. In a particular embodiment, the bacterium is a bacterium having a 16S rDNA molecule which is at least 70%, preferably at least 80% identical in sequence to a *Deinococcus* 16S rDNA sequence.

The invention also relates to the use of bacteria as defined above, especially in the pharmaceutical or agro-chemical industries.

In a particular embodiment, the invention relates to the use of bacteria as defined above for the production of a metabolite.

The invention also relates to a method for the production of a metabolite, the method comprising selecting a bacterium of this invention which produces said metabolite, culturing said bacterium, and collecting the metabolite from the culture medium.

In another particular embodiment, the invention relates to the use of bacteria as defined above for the production of a drug, vaccine or adjuvant.

The invention also relates to a method for the production of a drug, vaccine or adjuvant, the method comprising selecting a bacterium of the invention which produces said drug, vaccine or adjuvant, culturing said bacterium, and collecting the drug from the culture medium.

In another particular embodiment, the invention relates to the use of bacteria as defined above for the production of a recombinant protein.

In another particular embodiment, the invention relates to the use of bacteria as defined above for the production of an enzyme.

The invention also relates to a method for the production of a protein or an enzyme, the method comprising selecting a bacterium of the invention which produces said protein or enzyme, culturing said bacterium, and collecting the protein or enzyme from the culture medium.

More particularly, the invention relates to a method for the production of a metabolite, recombinant protein, enzyme, drug, vaccine or adjuvant, the method comprising:

Providing *Deinococcus* or related bacteria producing said metabolite, recombinant protein, enzyme, drug, vaccine or adjuvant;

Testing the size of the genome of said bacteria;

Selecting a bacterium having a genome size above 3.9 megabases;

Culturing said bacterium; and

Collecting the metabolite, recombinant protein, enzyme, drug, vaccine or adjuvant from the culture medium. In various embodiments of this method, the bacterium can have a genome size ranging from at least 3.9 megabases to about 10 megabases, at least 4 megabases to about 8 megabases, or at least 5 megabases to about 7.5 megabases. Other embodiments of this method utilize a bacterium having a genome size ranging from at least 3.9 megabases to 10 megabases, at least 4 megabases to 8 megabases, or at least 5 megabases to 7.5 megabases.

In a particular embodiment, said bacterium can utilize inulin and/or fiber cellulose as carbon source.

A further object of this invention is a method for modifying biomass, the method comprising exposing a biomass to a bacterium of the invention, or to an extract thereof.

The invention further relates to a method for modifying a biomass comprising inulin and/or fiber cellulose, the method comprising exposing said biomass to a bacterium having a genome size above 3.9 megabases, and (i) containing a 16S rDNA which, upon amplification using primers GTTAC-CCGGAATCACTGGGCGTA (SEQ ID NO: 1) and GGTATCTACGCATTCCACCGCTA (SEQ ID NO: 2), generates a fragment of about 158 base pairs and/or (ii) resisting a UV treatment of 4 mJ/cm$^2$ or to an extract thereof. In various embodiments of this method, the bacterium can have a genome size ranging from at least 3.9 megabases to about 10 megabases, at least 4 megabases to about 8 megabases, or at least 5 megabases to about 7.5 megabases. In various other embodiments of this method, the bacterium can have a genome size ranging from at least 3.9 megabases to about 10 megabases, at least 4 megabases to about 8 megabases, or at least 5 megabases to about 7.5 megabases.

The invention also relates to a method for producing a metabolite, recombinant protein, enzyme, drug, vaccine or adjuvant from a biomass comprising inulin and/or fiber cellulose, the method comprising contacting a *Deinococcus* bacterium having a genome size above 3.9 megabase with a biomass comprising inulin and/or fiber cellulose and recovering the metabolite, recombinant protein, enzyme, drug, vaccine or adjuvant. In various embodiments of this method, the *Deinococcus* bacterium can have a genome size ranging from at least 3.9 megabases to about 10 megabases, at least 4 megabases to about 8 megabases, or at least 5 megabases to about 7.5 megabases. In various embodiments of this method, the *Deinococcus* bacterium can have a genome size ranging from at least 3.9 megabases to about 10 megabases, at least 4 megabases to about 8 megabases, or at least 5 megabases to about 7.5 megabases.

In another particular embodiment, the invention relates to the use of bacterium as defined above for detoxification.

The invention also relates to a method for isolating a bacterium according to the invention, the method comprising:

a) providing a sample;

b) exposing the sample to an irradiation treatment;

c) selecting living bacteria from said exposed sample; and d) selecting, from said living bacteria, a bacterium which has a genome size above 3.9 megabase. In various embodiments of this method, the bacterium, optionally a *Deinococcus* bacterium, can have a genome size ranging from at least 3.9 megabases to about 10 megabases, at least 4 megabases to about 8 megabases, or at least 5 megabases to about 7.5 megabases. In various additional embodiments of this method, the bacterium, optionally a *Deinococcus* bacterium, can have a genome size ranging from at least 3.9 megabases to about 10 megabases, at least 4 megabases to about 8 megabases, or at least 5 megabases to about 7.5 megabases.

The invention also relates to a method for isolating a bacterium according to the invention, the method comprising:

a) providing a sample containing *Deinococcus* bacteria;

b) testing the size of the genome of bacteria in said sample; and b) selecting, from said sample, a *Deinococcus* bacterium which has a genome size above 3.9 megabase. In various embodiments of this method, the *Deinococcus* bacterium can have a genome size ranging from at least 3.9 megabases to about 10 megabases, at least 4 megabases to about 8 megabases, or at least 5 megabases to about 7.5 megabases. In various additional embodiments of this method, the *Deinococcus* bacterium can have a genome size ranging from at least 3.9 megabases to about 10 megabases, at least 4 megabases to about 8 megabases, or at least 5 megabases to about 7.5 megabases.

The invention also relates to a method for isolating a bacterium according to the invention, the method comprising:

a) providing a sample containing *Deinococcus* bacteria;

b) testing the level of genomic diversity of bacteria in said sample; and b) selecting, from said sample, a *Deinococcus* bacterium which has a level of genomic diversity greater than 15% greater than 25%, greater than 50% or ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

The invention also relates to a fermentor which comprises a bacterium of the invention in a culture medium.

DETAILED DESCRIPTION OF THE INVENTION

The invention describes the isolation and characterization of novel bacteria having the remarkable ability to degrade biomass and/or to produce bioenergy products, drugs or valuable metabolites.

DEFINITIONS

Genome Size

Genome size is the total amount of DNA contained within one copy of a genome. It is typically measured as the total number of nucleotide base pairs, typically in megabases (millions of base pairs, abbreviated Mb or Mbp). Methods of measuring the size of a genome are well known per se in the art. They include, without limitation, sequencing technologies, whole genome hybridization and Cot1/2 calculation (Chakrabarti S K et al Cellular and Molecular life science, 1984 40: 1290-1291), or pulse field electrophoresis (Chen H et al. Journal of bacteriology 1990, 190: 4206-4213).

Genomic Diversity

Genomic diversity designates the level of genetic material which an organism has acquired from another organism, without being the offspring of that organism. Genomic diversity may result from incorporation, through evolution, of genetic material by gene transfer, such as Horizontal gene transfer (HGT), also termed Lateral gene transfer (LGT). HGT or genomic diversity occurs or is detected when a gene or protein sequence from a particular organism has a stronger sequence similarity to a homolog from a very distant organism than it has with obviously closer relatives. The transfer of genetic material from a bacteria species to another can occur by several processes, including transformation, conjugation and/or transduction.

Transformation designates the uptake of naked DNA. It is common and can mediate the exchange of any part of a chromosome; this process mainly occurs in bacteria that are naturally transformable.

Conjugation is the transfer of DNA mediated by conjugal plasmids or conjugal transposons. It requires cell to cell contact but can occur between distantly related bacteria or even bacteria and eukaryotic cells.

Transduction refers to the transfer of DNA by phage. It requires that the donor and recipient share cell surface receptors for phage binding and thus is usually limited to closely related bacteria; the length of DNA transferred is limited by the size of the phage head.

The level of genomic diversity is measured as the % of genetic material in the genome which has been acquired through genetic transfer from distinct organisms. Prediction techniques to determine the % Genomic Diversity, or % HGT, include, without limitation, (i) codon determination, (ii) BLAST, (iii) gene distribution, and (iv) phylogenetics (Whitake J W et al., Biochemical Society Transactions 2009, 37:792-795).

Isolated

In relation to a bacterium, the term "isolated" indicates the bacterium is or has been cultivated, enriched, grown, amplified, selected, and/or characterized, or derives from a bacterium which has been cultivated, enriched, grown, amplified, selected, and/or characterized. An isolated bacterium, or its progeny, may be placed in different conditions or culture media, mixed with various substrates.

Metabolite

The term "metabolite" designates all possible intermediate molecules generated during a fermentation process, including but not limited to chemical products of industrial interest, such as organic acids, alcohols and building blocks.

Specific examples of organic acids include, more preferably, formate, acetate, lactate, butyrate, gluconate, xylonate, citrate, succinate, propionate, fumarate, malate, pyruvate, itaconic acid and kojic acid.

Specific examples of alcohols include more preferably ethanol, butanol, propanol, methanol, isopropanol, propanediol, glycerol, or 2-3 butane diol, preferably ethanol.

The metabolite may also have utility in cosmetics or agriculture, such as pigments, insecticides, pesticides, chemical-degrading compounds, etc.

Drug

The term drug designates, generally, any compound having a biological activity. This term includes any protein, polypeptide, peptide, chemical drugs, lipids, saccharides, etc., having a biological activity which may be used in the human or veterinary pharmaceutical industry. Examples of such drugs include, without limitation, antibiotics, hormones, bacteriostatic compounds, anti-metabolite agents, chemotherapeutic compounds, anti-fungal agents, anti-viral compounds, cytokine-activity compounds, cell-growth factors, vaccines and adjuvants.

Biomass

Within the context of the present invention, the term "biomass" refers to living and recently dead biological material that can be used as fuel or for industrial production. Most commonly, biomass refers to plant matter grown to generate electricity or produce biofuels, but it also includes plant or animal matter used for production of fibers, chemicals or heat. Biomass may also include biodegradable wastes that can be burnt as fuel. The term biomass does not include organic material which has been transformed by geological processes into substances such as coal or petroleum. Industrial biomass can be grown from numerous types of plants, including miscanthus, switch grass, hemp, sugarbeet, wheat, corn, poplar, willow, sorghum, sugarcane, and a variety of tree species, ranging from eucalyptus to oil palm.

The biomass according to the invention comprises raw biomass and/or secondary biomass. The raw biomass is unprocessed material from biological matter. Examples include forestry products, such as mature trees unsuitable for lumber or paper production, agricultural products, such as grasses, crops and animal manure, and aquatic products, such as algae and seaweed. The secondary biomass is any material initially derived from raw biomass, which has undergone significant chemical and physical changes. Examples include paper, leather, cotton, hemp, natural rubber products, food processing by-products, and used cooking oils.

The term lignocellulosic biomass according to the invention designates a raw biomass containing lignin, cellulose and/or xylan. The term lignocellulosic biomass thus essentially designates unprocessed material of biological origin, such as forestry products, including mature trees unsuitable for lumber or paper production, agricultural products, such as grasses, crops and animal manure, and aquatic products, such as algae and seaweed. Specific sources of biomass include, without limitation, hardwood or softwood stems, corn cobs, wheat straw, grass, leaves, seeds, paper, etc. (see for instance Sun et al., Bioresource Technology 83 (2002) 1-11). The term lignocellulosic biomass should be distinguished from transformed biomass or secondary biomass, which essentially contains hydrolysed pre-treated biomass products.

Examples of lignocellulosic biomass include wood or vegetal material derived from numerous types of plants, including miscanthus, switch grass, hemp, sugarbeet, wheat, corn, poplar, willow, sorghum, sugarcane, and a variety of tree species, ranging from eucalyptus to oil palm.

As used herein, the term "biomass derivatives" designates all molecules derived from raw biomass and/or from secondary biomass, as defined above, and in particular any material initially derived from raw biomass, which has undergone significant chemical and physical changes, such as for example, starch, cellulose, hemicelluloses and lignin.

Stress-Resistance

Within the context of this invention, the term "stress-resistant bacterium" designates a bacterium having the capacity to reassemble its genome, in full or in part, when disrupted by a stress. The stress may be any cell-destructing DNA damaging treatment, i.e., a treatment that is sufficient to cause 90% cell death, or more, in a culture of $E.\ coli$ bacteria. Even more preferably, the cell destructing DNA damaging treatment is a treatment that is sufficient to reduce by at least 2 log the bacterial titer in a culture of $E.\ coli$. Examples of such treatment include irradiation, preferably repeated irradiation, such as repeated and sequential UV irradiation, and/or the use of genotoxic agents. A preferred stress treatment is a UV treatment of between 0.5 and 400 mJ/cm2, more preferably of between 1 and 200 mJ/cm2, typically between 1 and 100 mJ/cm2, applied for a period of time of about 5" to 5'. A preferred UV treatment is 4 mJ/cm2 for 30 seconds, which may be repeated at an interval of between 1 and 8 hours, preferably 3 to 5 hours, and more preferably of about 4 hours.

About

The term "about" (or it synonyms such as "approximately") is used to describe a quantitative aspect of the invention that may be varied by up to 10%. Thus, the relevant quantitative aspect (e.g., genome size, genomic diversity, etc.) may be varied by ±10%. This term may be substituted by a particular quantitative value along with a percentage of variation ranging from 1% to 10% (e.g., a selected genome size±1%, ±2%, ±3%, ±4%, ±5%, ±6%, ±7%, ±8,%, ±9% or ±10%).

The invention now provides novel bacteria having unexpected properties and advantages. These bacteria have a surprisingly large genome and/or a surprisingly large level of genomic diversity, and exhibit advantageous properties for the production of compounds or activities in the fields of pharmaceutical and agro-chemical industries. More particularly, an object of this invention resides in an isolated bacterium, wherein said bacterium has a genome size above 3.9 megabases, and wherein said bacterium (i) contains a 16S rDNA which, upon amplification using primers GTTACCCGGAATCACTGGGCGTA (SEQ ID NO: 1) and GGTATCTACGCATTCCACCGCTA (SEQ ID NO: 2), generates a fragment of about 158 base pairs and/or (ii) resists a UV treatment of 4 mJ/cm$^2$. In various embodiments, the bacterium, optionally a *Deinococcus* bacterium, can have a genome size ranging from at least 3.9 megabases to 10 megabases, at least 4 megabases to 8 megabases, or at least 5 megabases to 7.5 megabases. In certain embodiments of this object of the invention, the isolated bacterium can also have a genomic diversity resulting from gene transfer that is greater than 15%, greater than 25%, greater than 50% or a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%.

Even more preferably, the genome of said bacterium has a size above 4.0 megabase, above 4.2 Mb, above 4.5 Mb, or even above 5 Mb. The discovery of such bacterium was totally unexpected considering the average genome of related strains, such as *Deinococcus* strains, is approx. 3.0 Mb.

Furthermore, the inventors have found bacteria having an extraordinary high level of genomic diversity, i.e., of genetic material acquired from diverse organisms. More particularly, the bacteria of this invention preferably have a genomic diversity greater than 15%, more preferably 25%, 30%, 40% or even above 50%. Other embodiments provide for bacteria having genomic diversity ranging from: at least 6% to 70%; at least 10% to 85%; at least 15% to 85%; at least 15% to 70%; at least 6% to 65%; at least 10% to 65%; at least 15% to 65%; or at least 15% to 65%. In certain embodiments of this object of the invention, the bacterium can also have a genomic diversity resulting from gene transfer that is greater than 15%, greater than 25%, greater than 50% or a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. In certain embodiments of this object of the invention, the bacterium can also have a genomic diversity resulting from gene transfer that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%. This property is particularly remarkable as the presence of diverse genetic material provides the bacteria with a broad spectrum of properties and activities.

A particular object of this invention is an isolated bacterium, wherein said bacterium contains a 16S rDNA which, upon amplification using primers GTTACCCGGAAT-CACTGGGCGTA (SEQ ID NO: 1) and GGTATCTACG-CATTCCACCGCTA (SEQ ID NO: 2), generates a fragment of about 158 base pairs, and wherein the genome of said bacterium comprises a genomic diversity resulting from gene transfer greater than 15%, greater than 25%, more preferably to 50% or ranging from: at least 6% to 70%; at least 10% to 85%; at least 15% to 85%; at least 15% to 70%; at least 6% to 65%; at least 10% to 65%; at least 15% to 65%; or at least 15% to 75%. In certain embodiments of this object of the invention, the bacterium can also have a genomic diversity resulting from gene transfer that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

The presence of the above mentioned 158 pb fragment is characteristic of bacteria that are related to *Deinococcus*. This feature, or the capacity to resist particular irradiation conditions as mentioned above, are additional features of the bacteria of this invention.

In a further embodiment, the bacterium may further comprise a recombinant nucleic acid molecule, i.e., a recombinant nucleic acid molecule introduced into said bacterium or an ancestor thereof. Such a recombinant nucleic acid is typically artificial, engineered to contain a particular gene or cluster, and comprised of DNA or RNA.

Even more particularly, the bacteria, in addition to the above properties, exhibit one or more or all of the following properties:

It is mesophile, i.e., can live, grow and exhibit functional properties at a temperature comprised between about 30° C. and 35° C., It is viable at a pH comprised between 4 and 9, It is viable in the presence of 2% ethanol, It can be grown in aerobiosis or in anaerobiosis, and/or It can utilize cellulose or a derivative thereof as carbon source.

Moreover, a preferred bacterium of this invention can further utilize additional substrates as carbon sources, particularly glucose, starch and sucrose. Preferred bacteria of this invention can also utilize carboxymethylcellulose, cellobiose, hemicellulose and xylose as carbon sources.

The bacteria may be cultivated and/or maintained in any suitable culture medium and device. Examples of such medium include complex glucose medium or defined medium as disclosed in the examples. Suitable medium are also commercially available.

Specific examples of bacteria of this invention are *Deinococcus* strains M1-3H and M23r-2A, or a derivative, mutant, transformant or progeny of said bacteria.

As disclosed in the examples, these strains are able to grow at a pH comprised between 5 and 9, and have a very large genome. Furthermore, these strains have a substantial genomic diversity, as measured by a % HGT above 15%, above 25% or ranging from: at least 6% to 70%; at least 10% to 85%; at least 15% to 85%; at least 15% to 70%; at least 6% to 65%; at least 10% to 65%; at least 15% to 65%; or at least 15% to 75%. In certain embodiments of this object of the invention, the bacterium can also have a genomic diversity, as measured by a % HGT, that is greater than 15%, greater than 25%, greater than 50% or a genomic diversity, as measured by a % HGT, ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

A further example of a bacterium of this invention is *Deinococcus* strain DRH048, or a derivative, mutant, transformant or progeny of said bacterium.

As disclosed in the examples, this strain is able to grow at a pH comprised between 5 and 9, and has a genome above 5.9 Mb. Furthermore, this strain has a very high level of genomic diversity, as measured by a % HGT above 60%, and is rifampycin resistant.

These mega*Deinococcus* bacteria are able to grow on all tested complex carbon sources, including inulin and fiber cellulose, which are raw and complex carbon sources. It should be noted that none of the tested *Deinococcus* bacteria having a regular genome size was able to use all of these carbon sources. None of the tested *Deinococcus* bacteria having a regular genome size was able to use inulin and fiber cellulose.

The tested mega*Deinococcus* bacteria were also able to use all tested nitrogen sources, including complex nitrogen sources, such as NaNO2.

It should be noted that the tested mega*Deinococcus* bacteria did not exhibit any auxotrophy for vitamins, and were able to grow on a medium devoid of Biotin, Niacin, Pyridoxin, Thiamin, and/or B12 vitamin. DRH048 is even able to grow on a vitamin-free medium.

Surprisingly and advantageously, the inventors have also discovered that the mega*Deinococcus* bacteria exhibit an increased number and diversity of genes involved in energetic metabolism. In comparison to *Deinococcus* bacteria having a regular genome size (an average genome size of about 3.0 megabases), preferred mega*Deinococcus* bacteria exhibit at least 15% to 60%, at least 15% to 50%, at least 15% to 45%, or at least 15% to 40% more genes involved in energetic metabolism, i.e., genes encoding proteins which are involved in biological pathways and reactions that contribute to creating or stocking energy products or metabolites in a cell. These include, without limitation, pathways and reactions such as biomass processing, e.g., the degradation of polymers of biomass into fermentable sugars; and sugars fermentation into valuable metabolites or products.

These bacteria of the present invention thus exhibit a combination of remarkable and unexpected properties, in relation to substrate utilization, metabolite production and genomic diversity which are particularly useful for industrial purposes. It should be understood that, using the teaching of the present invention and following experimental procedures as described e.g., in the experimental section, further bacteria, such as *Deinococcus* bacteria, having the properties according to this invention may be selected or isolated. In particular, now that the inventors have demonstrated the ability of certain *Deinococcus* or related bacteria to exhibit a large genome and high genomic diversity, the skilled person, following the protocols provided in the experimental section, can isolate other strains having such property.

In this regard, a further object of this invention is a method of isolating a bacterium, the method comprising:

Providing a sample that potentially contains bacteria;
Subjecting said sample to an irradiation treatment,
Isolating growing or living bacteria from said treated sample, and
Selecting, from said growing or living bacteria, a bacterium having a genome above 3.9 megabase.

The method can be implemented with various samples comprising uncharacterized bacteria, particularly with samples which are or derive from an environmental sample. Within the context of this invention, environmental samples include any sample containing (a plurality of) uncharacterized (micro)organisms, particularly uncultivated microorganisms (e.g., microorganisms that have not been purposely cultured and expanded in isolated form). The sample may be obtained or derived from natural environments or from artificial or specifically created environments.

As indicated, the sample may be any environmental sample, such as those obtained or derived from soil, water, vegetal extract, biological material, sediments, peatlands, industrial effluents or sites, mineral extracts, sand, and the like. The sample may be collected from various regions or conditions, such as but not limited to tropical regions, volcanic regions, forests, farms, industrial areas, etc. The sample usually contains various species of (uncharacterized, uncultivated) microorganisms, such as terrestrial microorganisms, marine microorganisms, freshwater microorganisms, symbiotic microorganisms, etc. Species of such environmental microorganisms include bacteria, algae, fungi, yeasts, moulds, viruses, etc. The microorganisms may include extremophile organisms, such as e.g., thermophiles. The sample typically comprises various species of such (uncultivated) microorganisms, as well as various amounts thereof. Furthermore, the sample may contain, in addition, known and/or cultivable microorganisms (e.g., prokaryotic or eukaryotic).

It should be understood that the present invention is not limited to any specific type of sample or environmental microorganism, but can be implemented using any sample comprising uncultivated microorganisms.

In a preferred embodiment, the sample is or derives from soil, water, hot springs, marine environment, mud, wood, stone, moss, vegetal extract, lichen, biological material, sediment, biofilm, industrial effluents, gas, sand, oil, sewage, or animal or human dejection.

For use in the present invention, the sample may be wet, soluble, dry, in the form of a suspension, paste, etc. Furthermore, prior to step b) of the method, the sample may be treated to improve the process, for instance to enrich for microorganisms, e.g., such as through filtration, washings, concentration, dilution, steering, drying, etc.

In a particular embodiment, the sample is in the form of a filtered suspension. More particularly, the sample may be sterile-filtered and/or placed in sterile water, prior to treatment step b).

Step b) of the process comprises subjecting the sample (i.e., microorganisms contained in the sample) to a cell destructing DNA damaging treatment, preferably an irradiation treatment, in particular a repeated irradiation treatment.

The cell destructing DNA damaging treatment designates a treatment that causes substantial cell death in the sample, as opposed to mere mutagenic treatments which introduce DNA modifications. In particular, the cell destructing DNA damaging treatment is a treatment that is sufficient to cause 90% cell death, or more, in a culture of *E. coli* bacteria. Even more preferably, the cell destructing DNA damaging treatment is a treatment that is sufficient to reduce by at least 2 log the bacterial titer in a culture of *E. coli*. The inventors have indeed demonstrated that the use of a cell destructing DNA damaging treatment allows the isolation and selection, with a high efficacy, of under-represented bacteria producing valuable metabolites.

The treatment preferably comprises subjecting the sample to irradiation(s) for a period of time sufficient to induce substantial cell death in the microorganisms present in the sample.

In a preferred embodiment, the treatment comprises subjecting the sample to one or several irradiations. A preferred treatment comprises subjecting the sample (i.e., microorganisms in the sample) to a repeated (e.g., sequential) irradiation treatment.

Irradiation may be selected from UV, gamma and/or X ray irradiation, either alone or in combinations, most preferably UV irradiation(s). Irradiation treatment typically comprises subjecting the microorganisms to one or several sequential irradiations (e.g., from 1 to 5), which may be of the same or different nature, preferably of the same nature. Repeated irradiation treatments are typically carried out at an interval of between 1 and 8 hours, preferably 3 to 5 hours, and more preferably of about 4 hours.

A particularly preferred treatment comprises subjecting the sample to a UV irradiation. The invention indeed shows that such a treatment allows to isolate with high efficacy from environmental (e.g., soil or water) samples, under-represented bacteria species producing metabolites. Irradiation treatments are typically of between 0.5 and 400 mJ/cm2, more preferably of between 1 and 200 mJ/cm2, typically between 1 and 100 mJ/cm2, applied for a period of time of about 5" to 5'. A preferred (UV) irradiation treatment is 4 mJ/cm$^2$.

In a specific embodiment, the treatment comprises subjecting the sample to at least 2, preferably at least 3 UV treatments of between 0.5 and 400 mJ/cm2 each, preferably of about 4 mJ/cm2 each, carried out at an interval of between 1 and 8 hours, preferably 3 to 5 hours, and more preferably of about 4 hours.

During the treatment phase, the sample is preferably placed in a suitable culture medium such as, without limitation, PGY (Bacto-peptone 10 g/L, Yeast extract 5 g/L, glucose 20 g/L) or LB (Bacto-tryptone 10 g/L, Yeast extract 2.5 g/L, Sodium chloride 10 g/L). It should be understood that other suitable culture media are known to the skilled person (Buchanan et al, 1974, Difco, 1995)) or may be prepared by the skilled person from such known media.

Treatment step b) is typically performed in a solid or semi-solid culture medium, such as in the presence of a gel (e.g., agar). A most preferred treatment medium comprises an agar culture medium, such as a soft agar medium. In a particular embodiment, a TGY agar medium is used to grow the bacteria. However, different solid media containing a carbon source, a nitrogen source and mineral salts can be used as well. Serial dilution techniques can also be used according to Schoenborn et al 2004.

In step c), living or growing bacteria are identified or isolated from the treated sample. Living or growing bacteria may be identified by different means known per se in the art. In a particular embodiment, colonies which form in the culture media are identified. The living or growing bacteria can be isolated and placed in fresh medium for further culture or expansion.

Step d) comprises selecting one or several bacteria having a desired genome size. This selection can be made using various techniques known per se in the art, such as pulse field electrophoresis, DNA hybridization and Cot ½ calculation, or genome sequencing.

In a particular embodiment, the invention relates to a method for isolating a bacterium according to the invention, the method comprising:

a) providing a sample containing *Deinococcus* bacteria;
b) testing the size of the genome of bacteria in said sample; and
c) selecting, from said sample, one or several *Deinococcus* bacteria having a genome size ranging from at least 3.9 megabases to 10 megabases, at least 4 megabases to 8 megabases, or at least 5 megabases to 7.5 megabases. In some aspects of this embodiment, In various embodiments of this method, the *Deinococcus* bacterium can have a genome size ranging from at least 3.9 megabases to about 10 megabases, at least 4 megabases to about 8 megabases, or at least 5 megabases to about 7.5 megabases.

The discovery of the existence of such bacteria was totally unexpected considering the average genome of *Deinococcus* strains is approx. 3.0 Mb.

In a particular embodiment of the invention, the above method further comprises a step of determining the level of genomic diversity in said bacteria and selecting bacteria having a genomic diversity greater than 15%, more preferably 25%, 30%, 40%, above 50% or a level of genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. The selected bacterium can also have a genomic diversity that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%. This property is particularly remarkable as the presence of diverse genetic material provides the bacteria with a broad spectrum of properties and activities.

In this regard, the invention also relates to a method for isolating a bacterium according to the invention, the method comprising:

a) providing a sample containing *Deinococcus* bacteria;
b) testing the genomic diversity of bacteria in said sample; and
c) selecting, from said sample, one or several *Deinococcus* bacteria having a genomic diversity greater than 15%, more preferably greater than 25%, 30%, 40% above 50% or having a genomic diversity ranging from: at least 6% to 70%; at least 10% to 85%; at least 15% to 85%; at least 15% to 70%; at least 6% to 65%; at least 10% to 65%; at least 15% to 65%; or at least 15% to 75%. The selected bacterium can also have a genomic diversity that is greater than 15%, greater than 25%, greater than 50% or a genomic diversity ranging from: at least 6% to about 70%; at least 10% to about 85%; at least 15% to about 85%; at least 15% to about 70%; at least 6% to about 65%; at least 10% to about 65%; at least 15% to about 65%; or at least 15% to about 75%.

The bacteria may further be selected or engineered for additional properties as mentioned above, i.e., the production of metabolites, drugs, enzymes, the modification of biomass, etc.

The selection or identification or bacteria producing a selected metabolite can be made according to techniques known per se in the art. In a particular embodiment, the identified or isolated bacteria can be exposed to one or several indicator cells followed by the selection of a bacterium which affect the viability, growth, metabolism, mobility, RNA expression, protein expression, protein secretion or virus production of at least one of said indicator cells.

In the case of antibiotic or antibiostatic agents, the indicator cells are typically reference bacterial strains and test bacteria which inhibit the growth or kill said reference strains are selected.

In the case of, e.g., anti-viral compounds, the indicator cells are typically virus-producing cells and bacteria which affect the production of virus or viability of virus-infected cells are selected.

In a particular aspect of the present invention, the bacteria are cultured under particular temperature conditions in order to identify or isolate bacteria which are viable or can be grown in a temperature range from approximately 4 to 70° C. More particularly, the bacteria are maintained at the selected temperature during step b), c) and/or d); and/or during an additional step e), in order to identify or isolate bacteria which are viable or can be grown at the desired temperature.

In another particular aspect of the present invention, the bacteria are cultured under particular saline conditions in order to identify or isolate bacteria which are viable or can be grown under concentration conditions of NaCl or equivalent salts possibly reaching around 5% weight/volume. More particularly, the bacteria are maintained at the selected salinity during step b), c) and/or d), and/or during an additional step e), in order to identify or isolate bacteria which are viable or can be grown at the desired salinity.

In a further particular and preferred embodiment of the present invention, the bacteria are cultured under particular pH conditions in order to identify or isolate bacteria which are viable or can be grown in a pH interval between approximately 3 and 9.5, preferably between 4 and 8. More particularly, the bacteria are maintained at the selected pH during step b), c) and/or d); and/or during an additional step e), in order to identify or isolate bacteria which are viable or can be grown at the desired pH.

In a further particular embodiment of the present invention, the bacteria are cultured under particular oxygenation conditions in order to identify or isolate bacteria which are viable or can be grown in aerobic and/or anaerobic conditions. More particularly, the bacteria are maintained under the selected oxygenation conditions during step b), c) and/or d); and/or during an additional step e), in order to identify or isolate bacteria which are viable or can be grown at the desired conditions.

In a further particular embodiment of the present invention, the bacteria are cultured in a particular culture medium in order to identify or isolate bacteria which are viable or can be grown in the presence of a selected carbon source. More particularly, the bacteria are maintained under the medium during step b), c) and/or d); and/or during an additional step e), in order to identify or isolate bacteria which are viable or can be grown using the desired carbon source.

It should be understood that the above characteristics can be selected individually or in any combinations. For instance, the method can be used to identify bacteria which are viable or can be grown at a desired temperature and salinity, or at a desired temperature and pH, or at a desired temperature, pH and oxygenation condition. Furthermore, the methods of this invention may comprise a further step of modifying, e.g., either biologically, genetically and/or chemically, the bacteria, or their DNA, by any process known per se in the art, said modification aiming e.g., to improve the viability, growth or functions of the said bacterium, e.g., in order to improve the antibiotic activity. Such modification step includes, without limitation, cell fusion, accelerated evolution, DNA shuffling, mutagenesis, insertion of eukaryote, prokaryote or synthetic nucleic acid (e.g., DNA) from another strain, or any genetic engineering technology. The modification may also include a step of introducing a marker gene (e.g., kanamycin resistance) in the bacterium.

The selection of bacteria having the ability to modify biomass can be made by exposing the bacteria to a biomass and selecting cells which degrade biomass and/or by selecting cells which can use particular carbon sources such as lignin, xylan, cellulose, etc.

A further object of the invention is an extract of a bacterium as defined above. An "extract of a bacterium" designates any fraction obtained from a bacterium, such as a cell supernatant, cell debris, cell walls, DNA extract, enzymes or enzyme preparation or any preparation derived from bacteria by chemical, physical and/or enzymatic treatment, which is essentially free of living bacteria.

The invention also relates to derivatives, transformants, mutants or progeny of a bacterium as described above. The term "transformant" designates a strain which contains a recombinant nucleic acid (i.e., a nucleic acid that is not naturally present in said bacterium, or that has been altered or duplicated). The term mutant designates a strain which results from a mutagenic treatment. Derivatives designate any strain obtained from a strain of the present invention, e.g., by selection, which retains the property of having a large genome and/or substantial genomic diversity.

A further object of the invention relates to the use of a bacterium as defined above for producing an organic acid or alcohol.

A further of object of the present invention relates to the use of a bacterium as defined above for producing bioalcohol, preferably ethanol.

The invention also relates to a method of producing an alcohol, preferably ethanol comprising cultivating a bacterium as defined above in the presence of an appropriate substrate, and collecting the alcohol.

The substrate may be any culture medium or various types of biomass or products derived therefrom. In particular, said acids and alcohols may be produced from renewable resources, especially plant or animal biomass, or from municipal and industrial wastes.

A particular object of the invention relates to a method for producing a bioalcohol, comprising exposing a biomass to a bacterium of this invention, or an extract thereof, and, optionally, collecting the bioalcohol.

The bioalcohol is preferably ethanol.

The method of the invention may be performed in a reactor of conversion. By "reactor" is meant a conventional fermentation tank or any apparatus or system for biomass conversion specially designed to implement the invention and therefore consisting in particular of bioreactors, biofilters, rotary biological contactors, and other gaseous and/or liquid phase bioreactors, especially those adapted for the treatment of biomass or biomass derivatives. The apparatus which can be used according to the invention can be used continuously or in batch loads.

In the reactor, to implement the method of the invention, at least one bacterium of the invention, or bacterial extract thereof, is used, whilst said reactor is arranged and supplied so that physicochemical conditions are set up and maintained therein so that said bacterium is operational for the application under consideration and so that, optionally, bacterial growth is possible and preferably promoted therein.

The process may be conducted under aerobiosis, anaerobiosis or under microaerobiosis, depending on the substrate and bacterium.

Further aspects and advantages of the invention will be disclosed in the following examples, which should be considered as illustrative and do not limit the scope of this application.

EXAMPLES

A. Materials

Culture Media
167 Thermus Medium

| | |
|---|---|
| Tryptone | 1 g |
| Yeast extract | 1 g |
| Agar | 28 g |
| Nitrilotriacetic acid | 100 mg |
| $CaSO_4 \times 2\,H_2O$ | 40 mg |
| $MgCl_2 \times 6\,H_2O$ | 200 mg |
| 0.01M Fe citrate | 0.5 ml |
| Solution of trace elements (see below) | 0.5 ml |
| Phosphate buffer (see below) | 100 ml |
| $H_2O$ | 900 ml |
| Adjust to pH 7.2 with NaOH, autoclave at 121° C. for 15 min. autoclave the phosphate buffer separately and add to the medium | |

Phosphate Buffer

| | |
|---|---|
| $KH_2PO_4$ | 5.44 G |
| $Na_2HPO_4 \times 12\,H_2O$ | 43 G |
| $H_2O$ | 1000 Ml |
| Adjust to pH 7.2 | |

Minimum Medium

MOPS Buffer

| | |
|---|---|
| MOPS acid | 400 mM |
| $NH_4Cl$ | 200 mM |
| NaOH | 100 mM |
| KOH | 100 mM |
| $CaCl_2$ | 5 M |
| $K_2SO_4$ | 276 mM |
| $MgCl_2$ | 5.28 mM |
| pH 7, filtered, sterilised | |

This media is supplemented with the appropriate carbon source (glucose (0.1 to 10%,) carboxymethyl cellulose (0.1 to 10%,), xylan (0.1 to 10%,), xylose (0.1 to 10%,) . . . ).

B. Isolation of UV-Resistant Bacteria from Water Samples

Water samples were concentrated by filtration over a 0.22 μm nitrocellulose filter (Millipore, France), then placed in suspension in 10 ml of sterile water. The filtered solution is then sonicated for approximately 60 seconds to resuspend the bacteria.

Following sonication, between 150 μl and 2 ml of the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l, and yeast extract (Fluka, France) 5 g/l. The seeded culture media then undergo 3 UV treatments using a BLX-E254 biolink (Vilber-Lourmat, France) of 4 mJ/cm2 each, carried out at an interval of 4 hours. After incubation at 30 to 50° C. for 3 to 4 days, the viable colonies of interest were visible.

C. Isolation of UV-Resistant Bacteria from Wood and Pebble Samples

Wood and pebble samples were immersed in sterile water then vortexed and sonicated for approximately 60 seconds.

Following sonication, between 150 μl and 2 ml of the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l, and yeast extract (Fluka, France) 5 g/l. The seeded culture media then undergo 3 UV treatments using a BLX-E254 biolink (Vilber-Lourmat, France) of 4 mJ/cm2 each, carried out at an interval of 4 hours. After incubation at 30 to 50° C. for 3 to 4 days, the viable colonies of interest were visible.

D. Identification of Mega-*Deinococcus*

2 mL UV-resistant pink bacterial cultures are obtained after 3 days of growth at 45° C. on rich medium. Microscopic observations show that cultures are composed by coccoïd cells. On this type of cells, DNA extraction is performed as follow: After centrifugation of 400 μL-culture at 8000 g for 5 minutes, supernatant is discarded. The pellet is suspended with 100 μL of sterile water and 40 μL EDTA at 12.5 mM. After incubation at 37° C. for 1 hour, 10 μL NaOH at 0.1 M is added. The preparation is then heated at 100° C. for 5 minutes. After centrifugation at 8000 g for 3 minutes, supernatant is collected (100-150 μL) and diluted v/v within sterile water.

To detect thermophile Deinococci, primers DeinoF1 (5'GTT ACC CGG AAT CAC TGG GCG TA3'—SEQ ID NO: 1) and DeinoR3 (5'GGT ATC TAC GCA TTC CAC CGC TA3'—SEQ ID NO: 2) amplify a region of 158 bp of 16S rDNA. The 50 μL-PCR mixture is composed by 2 U of Taq polymerase, 5 μL of Taq buffer containing $MgCl_2$, 0.5 μL of dNTP at 10 mM, 2.25 μL of each primers at 10 μM, 0.5 μL DNA and sterile $H_2O$ qsp 50 μL.

The PCR program is an initial denaturation step of 5 minutes at 95° C., 30 cycles of denaturation of 30 seconds at 94° C., annealing of 30 seconds at 70° C. and elongation of 45 seconds at 72° C., followed by a final elongation of 10 minutes at 72° C.

5 μL of PCR products are deposited on 1% agarose gel containing ethydium bromide. PCR bands are visualized under UV light. The presence of a major band at 158 bp indicates that the PCR product corresponds to *Deinococcus* partial 16S rDNA.

Figure 1:
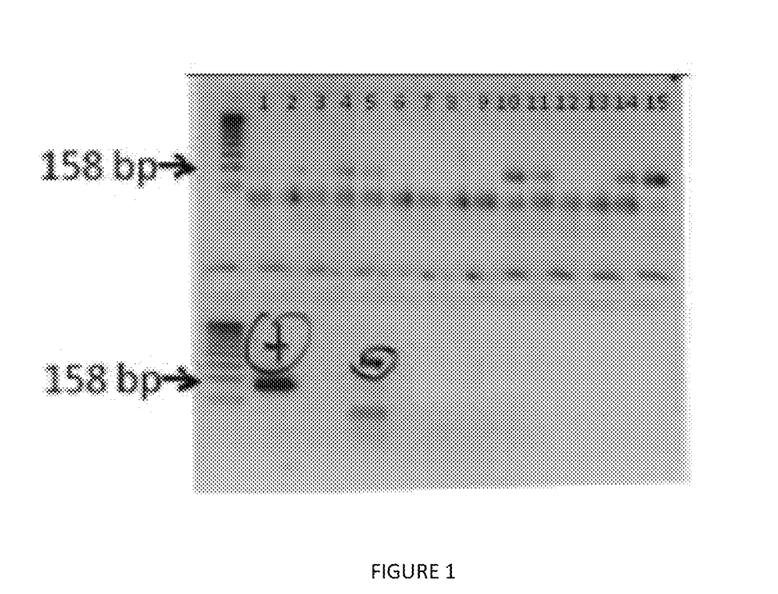
FIG. 1: PCR performed with primers DeinoF1 and DeinoR3. Lanes 4, 5, 10, 11, 14 and 15 are *Deinococcus* strains, Lanes 1 to 3, 6 to 9, 12 and 13 are not *Deinococcus* strains.

The results presented in FIG. 1 show bacteria that amplify a 158 bp fragment have been isolated from the treated sample.

Genomic DNA was extracted using the Macherey-Nagel NUCLEOSPIN Tissue kit. Genomic DNA was then submitted to sequencing using the Solexa technology (Solexa Inc. BioTechniques, December 2006: p29). We have obtained a coverage of 100 to 250, with $5 \times 10^6$ to $15 \times 10^6$ reads.

The size of the bacterial genome was then determined. Bacteria having unexpectedly large genomes are reported in table 1 below, in comparison to reference bacteria.

TABLE 1

|  | Genome size |
| --- | --- |
| *Deinococcus geothermalis* DSM 11300 | 3247018 |
| *Deinococcus radiodurans* R1 | 3284088 |
| M1-3H | 4031129 |
| M23r-2A | 3619528 |

*Deinococcus* bacteria were subjected to a UV treatment of 4 $mJ/cm^2$, cultivated in a rifampycin-containing medium (10 to 100 μg/ml). Bacteria able to grow on rifampycin were then isolated and the size of their genome was measured as disclosed above.

*Deinococcus* DRH048 was identified and selected, having a genome size of approx. 5,980 Mb.

E. Identification of Xeno-*Deinococcus*

Genomic variation in closely related species cannot be explained by vertical descent alone, and HGT is a major evolutionary factor to be considered. HGT is the acquisition of foreign genes by any genome either by transformation, transduction, or conjugation. HGT is suggested when a gene or protein sequence from a particular organism has a stronger sequence similarity to a homolog from a very distant organism than it has with obviously closer relatives. The level of genomic diversity in the identified bacterial strains has been determined and is represented in the following Table 2:

TABLE 2

|  | Origin of the HGT | Phylum | % Genomic diversity |
| --- | --- | --- | --- |
| M1-3H | *Burkholderia pseudomalle* | Beta Proteobacteria | 18 |
|  | *Herpetosiphon aurantiacus* | Chlorofexi |  |
|  | *Syntrophobacter fumaroxidans* | Delta proteobacteria Actinobacteria |  |
|  | *Rubrobacter xylanophilus* | Actinobacteria |  |
|  | *Frankia sp* |  |  |
| M23r-2A | *Burkholderia pseudomalle* | Beta Proteobacteria | 28 |
|  | *Verminephrobacter eiseniae* | Beta proteobacteria |  |
|  | *Acidovorax avenae* | Beta proteobacteria |  |
|  | *Polaromonas sp* | Beta proteobacteriaa |  |
|  | *Frankia sp* | Actinobacteria |  |
| DRH38 | *Burkholderia pseudomalle* | Beta Proteobacteria | 9 |
|  | *Anthrobacter sp* | Actinobacteria |  |
|  | *Pelotomaculum thermopropionicum* | Firmicute Beta proteobacteriaa |  |
|  | *Polaromonas sp* | Actinobacteria |  |
|  | *Frankia sp* |  |  |
| M11-12B | *Burkholderia pseudomalle* | Beta Proteobacteria | 16 |
|  | *Herpetosiphon aurantiacus* | Chlorofexi |  |
|  | *Chloroflexus aggregans* | Chlorofexi |  |
|  | *Aromatoleum aromaticum* | belta proteobacteriaa |  |
|  | *Physcomitrella patens* | Bryophyte |  |

TABLE 2-continued

| | Origin of the HGT | Phylum | % Genomic diversity |
|---|---|---|---|
| DRH048 | Burkholderia pseudomalle | Beta Proteobacteria | 64 |
| | Herpetosiphon aurantiacus | Chlorofexi | |
| | Paenibacillus sp. | Firmicute | |
| | Myxococcus xanthus | delta proteobacteriaa | |
| | Nostoc punctiforme | cyanobacteria | |

F. Metabolic Pathways

In addition to a high level of genomic diversity, the inventors have also discovered that mega*Deinococcus* bacteria exhibit an increased number and diversity of genes involved in energetic metabolism. In comparison to *Deinococcus* bacteria having a regular genome size, some tested mega*Deinococcus* bacteria exhibit at least 15%, more preferably at least 25%, 40% or even at least 50% more genes involved in energetic metabolism. Such an increased number of genes shall confer on the bacteria advantageous properties.

More particularly, there is a direct relationship between the genome size and the diversity of metabolic pathways found in mega*Deinococcus*. MegaDeinococcus exhibit a combination of remarkable and unexpected properties, in relation to substrate utilization which are correlated to their genome size.

The following experimentations compare the substrates utilization capability of 4 mega*Deinococcus* having a genome size above 3.9 megabases with 4 *Deinococcus* having a smaller genome below 2.9 megabases, using commercialized galleries API50CH.

About 10 ml pre-cultures of *Deinococcus* sp. (Four Mega *Deinococcus* whose genome size is above 3.9 megabases: *D. grandis* M5-5A, *D. misasensis* DSM22238, *D. geothermalis* M36-8C and *D. guilhemensis* M1-3H and three *Deinococcus* with smaller genomes: *D. geothermalis* M31-8F, *D. murrayi* M11-12B, *D. murrayi* MC3-9A and *D. murrayi* M13-1A) are each performed in complex medium glucose CMG1% (Peptone 2 g/L; Yeast Extract 5 g/L; Glucose 55 mM (10 g/L); MOPS acid 40 mM; $NH_4Cl$ 20 mM; NaOH 10 mM; KOH 10 mM; $CaCl_2.2H_2O$ 0.5 µM; $Na_2SO4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; Pyridoxin (pyridoxal HCl ou vitamine B6) 1 µg/L; Thiamin HCl (vitamine B1); $FeCl_3$ 20 µM; Sodium Citrate.$2H_2O$ 20 µM; $K_2HPO_4$ 5.7 mM).

When pre-cultures reached stationary phase, bacteria are harvested by centrifugation and washed three times with sterile osmosed water. Pellet is taken in 10 ml medium API 50 CHL whose composition is given by the manufacturer.

About 200 µl bacteria are loaded in galleries API 50 CH commercialized by Biomérieux (reference: 50410). The galleries are incubated at the corresponding temperature of growth of *Deinococcus* sp., during 48 and 72 hours.

During incubation, fermentation is revealed by color changed in the tube caused by production of acid and detected by the pH indicator present in medium.

Sugars assimilation is revealed by bacteria growth as the substrate is used as sole carbon source. Therefore, total number of sugars metabolized was counted for each bacterium after 48 and 72 hours (FIG. 2).

These experimentations demonstrate that MegaDeinococcus of the invention, whose genome size is above 3.9 megabases, are able to assimilate a greater diversity of substrates than *Deinococcus* with smaller genomes (FIG. 2), indicating that these megagenomes display a greater metabolic diversity.

Figure 2:
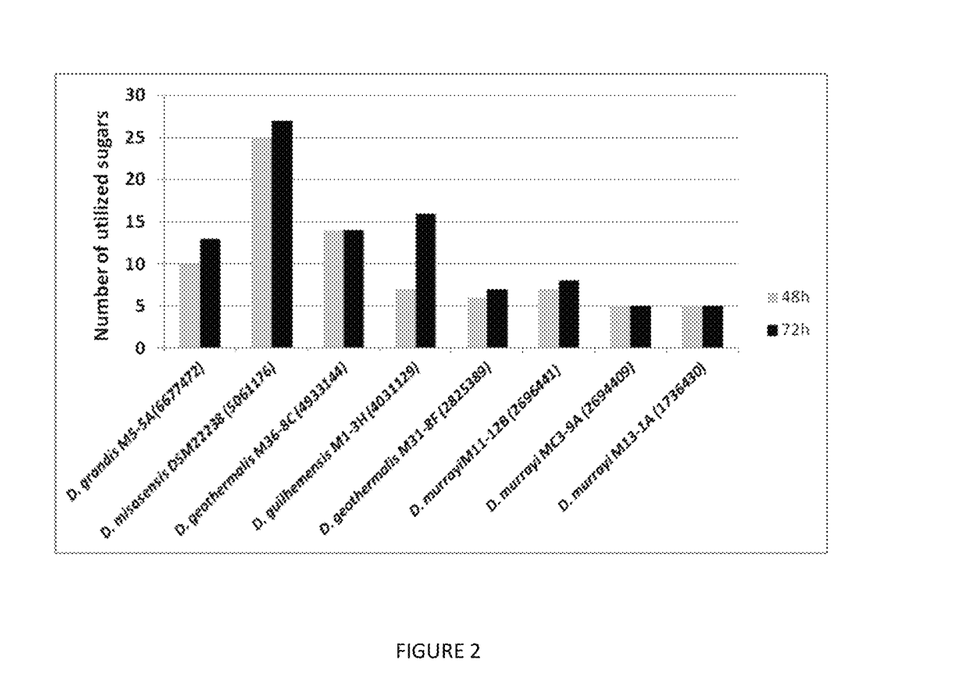
FIG. 2: Bar graph illustrating the ability of *Deinococcus* sp. to utilize several sugars at the temperature of growth of bacteria, after 48 and 72 hours. The *Deinococcus* genome sizes are indicated in bracket and expressed in base pairs. Total number of sugars metabolized is counted for each bacterium from galleries API wherein said bacteria are cultivated.
Figure 3A:
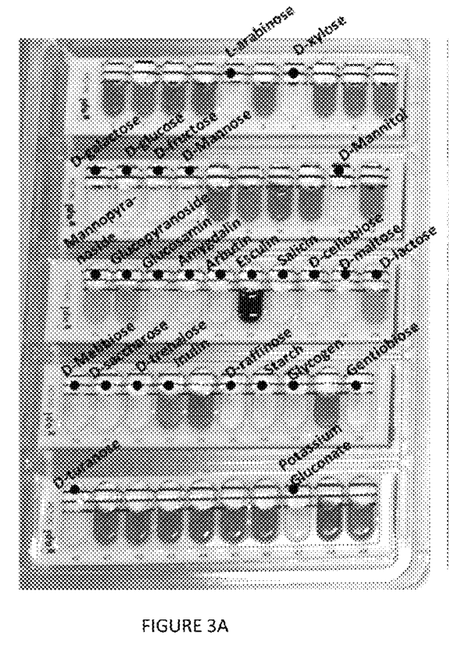
FIGS. 3A-3B: Galleries API 50CH (Biomérieux). A. *Deinococcus D. misasensis* DSM22238 having a mega genome (5061176 base pairs). B. *Deinococcus murrayi* M13-1A with genome size of 1736430 base pairs. Only substrates that are utilized during fermentation by bacteria are indicated by a black dot.
Figure 3B:
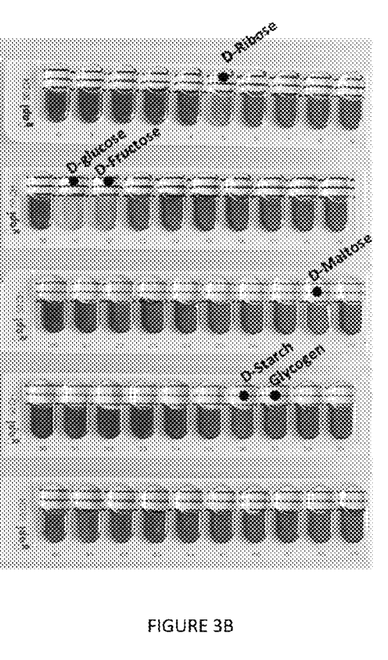

In particular, *D. misasensis* DSM22238 with genome size of 5061176 base pairs is able to utilize more than 50% of the studied substrates whereas *D. murrayi* M13-1A with genome size of 1736430 base pairs utilizes only 10% (FIGS. 2 & 3). More precisely, *D. misasensis* DSM22238 is able to metabolize representative sugars from biomass (hexoses: D-glucose, fructose and pentoses: L-arabinose, D-xylose), to ferment degradation product of cellulose (cellobiose), but also more complex carbohydrates polymers such as inulin and starch (FIG. 3).

Furthermore mega*Deinococcus*, are also able to use D-xylose, D-galactose, D-turanose, and more exotic or rare substrates like salicin, esculin and amygdalin (FIG. 3).

G: Inulin Consumption

The inventors have discovered that MegaDeinococcus bacteria are also able to use inulin as sole carbon source, unlike *Deinococcus* with smaller genome size.

Figure 4:
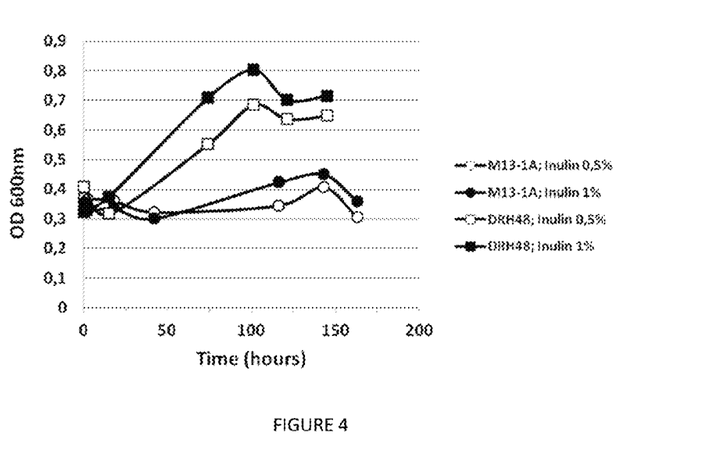
FIG. 4: Graphic showing the growth of *Deinococcus* DRH048 (MegaDeinococcus) and *Deinococcus* M13-1A (small genome) on defined medium containing inulin (0.5% or 1 w/v %) as sole carbon source.

The following experimentations demonstrate the ability of megagenome *Deinococcus* sp. to grow on minimal medium containing inulin as sole carbon source compared to *Deinococcus* whose genome is markedly smaller (FIG. 4).

Pre-cultures of *Deinococcus* sp (megagenome *Deinococcus* DRH048 of 5938218 base pairs and *Deinococcus* M13-1A of 1736430 base pairs) are each performed in 20 ml of complex medium glucose CMG1% (Peptone 2 g/L; Yeast Extract 5 g/L; Glucose 55 mM (10 g/L); MOPS acid 40 mM; $NH_4Cl$ 20 mM; NaOH 10 mM; KOH 10 mM; $CaCl_2.2H_2O$ 0.5 µM; $Na_2SO4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; Pyridoxin (pyridoxal HCl ou vitamine B6) 1 µg/L; Thiamin HCl (vitamine B1); $FeCl_3$ 20 µM; Sodium Citrate.$2H_2O$ 20 µM; $K_2HPO_4$ 5.7 mM) until bacteria reach stationary phase.

Bacteria are then harvested by centrifugation.

Bacteria pellets are washed with sterile deionized water and taken in a volume in such away $OD_{600nm}$ is equal to 2.

Then, 5 ml of each washed pre-cultures are used to inoculate 45 ml of defined minimal medium containing inulin (0.5 or 1 w/v %) as sole carbon source (Inulin 10 g/L or 5 g/L; MOPS acid 40 mM; $NH_4Cl$ 20 mM; NaOH 10 mM; KOH 10 mM; $CaCl_2.2H_2O$ 0.5 µM; $Na_2SO4.10H_2O$ 0.276 mM; $MgCl_2.6H_2O$ 0.528 mM; $(NH_4)_6(Mo_7)O_{24}.4H_2O$ 3 nM; $H_3BO_3$ 0.4 µM; $CoCl_2.6H_2O$ 30 nM; $CuSO_4.5H_2O$ 10 nM; $MnCl_2$ 0.25 µM; $ZnSO_4.7H_2O$ 10 nM; D-Biotin 1 µg/L; Niacin (nicotinic acid) 1 µg/L; Pyridoxin (pyridoxal HCl ou vitamine B6) 1 µg/L; Thiamin HCl (vitamine B1); $FeCl_3$ 20 µM; Sodium Citrate.$2H_2O$ 20 µM; $K_2HPO_4$ 5.7 mM).

Growth is performed in 250 ml erlen meyer and are followed by measuring $OD_{600nm}$.

Dosage of inulin is performed thanks to enzymatic assays as follow: 0.5 ml of culture is incubated at 37° C., 4 h with 0.5 ml of inulinase from *Aspergilus niger* (Sigma Aldrich, 57620-50MG-F) at concentration of 0.1 mg/ml (2.5 U/ml). The realized fructose is then quantified on dionex.

These experimentations demonstrate that megagenome *Deinococcus* bacteria are able to use inulin as sole carbon source. More particularly, FIG. 4 illustrates the ability of DRH048 to grow on minimal medium containing either 0.5 or 1 (w/v) % of inulin as sole carbon source unlike smaller genome *Deinococcus* M13-1A.

Figure 5:
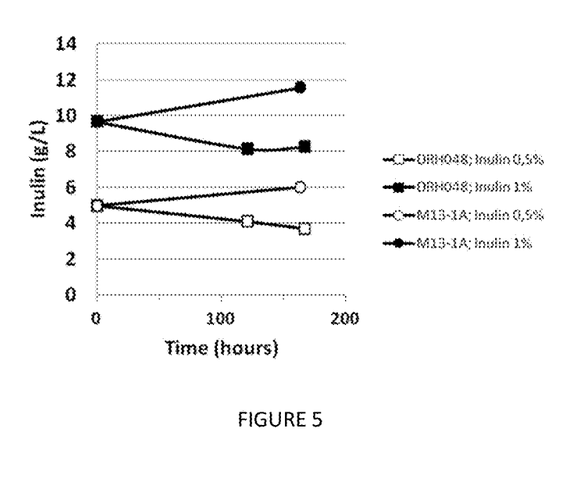
FIG. 5: Graphic showing the inulin consumption (g/l) by *Deinococcus* DRH048 throughout the growth when the bacterium is cultivated in defined medium containing inulin (0.5% or 1%) as sole carbon source. Control is the inulin concentration which has been monitored in a culture of *D. murrayi* M13-1A which does not hydrolyze and metabolize inulin.

In addition, the concentration of inulin decreases during the growth of DRH048 (FIG. 5) while free fructose which might be released from inulin after enzymatic attacks by bacteria are not detected in the culture medium under a free form.

Taken together, these data indicate that DRH048 is able to hydrolyze inulin and to consume the degradation products (fructose) rapidly after enzymatic hydrolysis of the polymer. The slightly increase of inulin concentration observed for M13-3A (FIG. 5) is due to a concentration of this carbon source generated by a slight evaporation of the culture medium when prolonged culture time are performed. This phenomenon is not observed for DRH048 due to a significant consumption of the carbon source.

H. Properties of Mega-*Deinococcus* Bacteria

Bacteria of the invention having a megagenome and/or a high level of genomic diversity were tested under different conditions to evaluate their functional properties.

The results show that such bacteria indeed have improved biological activities, which are correlated to their genome size and diversity. In particular, 21 bacteria were cultivated in a defined medium in the presence of different carbon sources and tested for their ability to efficiently grow. One of these tested bacteria was MegaDeinococcus bacterium DRH048, while the other 20 had a genome size below 3.5 Mb.

The results obtained show that the megaDeino bacterium is the only one able to utilize all tested complex and diverse substrates as carbon sources, namely glucose, CMC, cellobiose, xylan, xylose, glycerol, sucrose, starch, fructose, peptone, inulin and fiber cellulose. Notably, DRH048 is the only bacterium able to use CMC.

The mega*Deinococcus* bacterium was also able to degrade Whatman paper (fiber cellulose), while 15% only of *Deinococcus* with normal genome size responded to this test.

The mega*Deinococcus* bacterium was also able to use Inulin as carbon source, while 5% only of *Deinococcus* with normal genome size responded to this test.

Significantly, the mega*Deinococcus* bacteria are the only one having the ability to use all tested complex carbon sources such as Inulin and fiber cellulose. 0% tested *Deinococcus* with normal genome size responded to these two tests.

The mega*Deinococcus* bacterium was also able to grow in a culture medium lacking biotin, niacin, pyridoxine, thiamin, vitamin B12, as well as in a vitamin-free medium.

The mega*Deinococcus* bacterium was also able to use all tested nitrogen sources, including $NH_4Cl$, urea, $NaNO_3$, $NaNO_2$, and glutamate.

The invention claimed is:

1. A method for the production of a metabolite, recombinant protein, enzyme, drug, vaccine or adjuvant, the method comprising
    providing *Deinococcus* bacteria producing said metabolite, recombinant protein, enzyme, drug, vaccine or adjuvant;
    measuring the size of the genome of said bacteria;
    selecting a *Deinococcus* bacterium having a measured genome size above 3.9 megabases;
    culturing said selected *Deinococcus* bacterium in a culture medium; and
    collecting the metabolite, recombinant protein, enzyme, drug, vaccine or adjuvant from the culture medium.

2. The method of claim 1, wherein the step of selecting comprises selecting the *Deinococcus* bacterium having a measured genome size above 4.0 megabases.

3. The method of claim 1, wherein the genome of said selected *Deinococcus* bacterium comprises a genomic diversity selected from the group consisting of greater than 15%, greater than 25%, and greater than 50%.

4. The method of claim 1, wherein said *Deinococcus* bacteria are obtained by a method comprising the following steps:
    a) providing a sample comprising bacteria;
    b) exposing the sample to an irradiation treatment; and
    c) culturing said irradiated sample and isolating living *Deinococcus* bacteria from said sample.

5. The method of claim 1, wherein said *Deinococcus* bacterium further comprises a recombinant nucleic acid molecule.

6. The method of claim 1, wherein said *Deinococcus* bacterium is modified by accelerated evolution, by DNA shuffling technologies, by insertion of eukaryote, prokaryote or synthetic non-*Deinococcus* DNA, or by insertion of another *Deinococcus* strain DNA.

7. The method of claim 1, wherein said *Deinococcus* bacterium is a mesophile, is viable at a pH between 4 and 9, and/or is viable in the presence of 2% ethanol and/or wherein said *Deinococcus* bacterium can be grown in aerobiosis or in anaerobiosis.

8. The method of claim 1, wherein said *Deinococcus* bacterium utilizes inulin and/or fiber cellulose as a carbon source.

9. A method for isolating a bacterium, the method comprising:
 a) providing a sample that potentially contains bacteria;
 b) exposing the sample to an irradiation treatment;
 c) selecting living bacteria from said exposed sample;
 d) measuring the size of the genome of said bacteria; and
 e) selecting, from said living bacteria, a *Deinococcus* bacterium which has a genome size above 3.9 megabases.

10. The method of claim 9, wherein step b) comprises exposing the sample to a UV treatment of 4 $mJ/cm^2$.

11. A method for isolating a *Deinococcus* bacterium, the method comprising the following steps:
 a) providing a sample containing *Deinococcus* bacteria;
 b) measuring the size of the genome of said *Deinococcus* bacteria; and
 c) selecting, from said sample, one or several *Deinococcus* bacteria having a measured genome size above 3.9 megabases and, optionally, having a genomic diversity above 15%.

12. The method of claim 1, wherein said measuring comprises sequencing the genome of said *Deinococcus* bacterium.

13. The method of claim 1, wherein said measuring comprises whole genome hybridization and Cotl/2 calculation.

14. The method of claim 1, wherein said measuring comprises pulsed field electrophoresis.

* * * * *